United States Patent
Colvin et al.

(10) Patent No.: US 8,197,538 B2
(45) Date of Patent: Jun. 12, 2012

(54) ANNULOPLASTY PROSTHESIS WITH IN VIVO SHAPE IDENTIFICATION AND RELATED METHODS OF USE

(75) Inventors: Stephen B. Colvin, New York, NY (US); Aubrey Galloway, Bronxville, NY (US); Eugene Grossi, New York, NY (US); Timothy R. Ryan, Shorewood, MN (US)

(73) Assignee: Medtronic, Inc., Minneapolis, MN (US)

(*) Notice: Subject to any disclaimer, the term of this patent is extended or adjusted under 35 U.S.C. 154(b) by 256 days.

(21) Appl. No.: 11/809,221

(22) Filed: May 31, 2007

(65) Prior Publication Data

US 2007/0299514 A1    Dec. 27, 2007

Related U.S. Application Data

(60) Provisional application No. 60/810,599, filed on Jun. 2, 2006.

(51) Int. Cl.
*A61F 2/24* (2006.01)
(52) U.S. Cl. ............... 623/2.36; 623/2.37; 623/1.26; 623/1.24
(58) Field of Classification Search .......... 623/1.34, 623/2, 2.11, 1.24, 1.26, 2.36–2.37
See application file for complete search history.

(56) References Cited

U.S. PATENT DOCUMENTS

| | | |
|---|---|---|
| 3,656,185 A | 4/1972 | Carpentier |
| 3,966,401 A | 6/1976 | Hancock et al. |
| 4,050,893 A | 9/1977 | Hancock et al. |
| 4,055,861 A | 11/1977 | Carpentier et al. |
| 4,164,046 A | 8/1979 | Cooley |
| 4,182,446 A | 1/1980 | Penny |
| 4,917,698 A | 4/1990 | Carpentier et al. |
| 5,011,481 A | 4/1991 | Myers et al. |
| 5,041,130 A | 8/1991 | Cosgrove et al. |
| 5,061,277 A | 10/1991 | Carpentier et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,350,420 A | 9/1994 | Cosgrove et al. |
| 5,376,112 A | 12/1994 | Duran |
| 5,496,336 A | 3/1996 | Cosgrove et al. |
| 5,522,884 A | 6/1996 | Wright |

(Continued)

FOREIGN PATENT DOCUMENTS

EP    0 257 874    6/1987
(Continued)

OTHER PUBLICATIONS

US 6,197,052, 3/2001, Cosgrove et al. (withdrawn).
(Continued)

*Primary Examiner* — Thomas J Sweet
*Assistant Examiner* — Seema Swaminathan

(57) ABSTRACT

An annuloplasty prosthesis including a sheath, an arcuate stiffening element, and an imaging element. The arcuate stiffening element is disposed within the sheath and defines discrete, first and second ends separated by a lateral spacing. The imaging element is disposed within the sheath along the lateral spacing. With this configuration, following implant to the valve annulus, the imaging element provides a mechanism for non-invasively evaluating a shape of the valve annulus, for example, via radiographic, echogenic and/or other image enhancing visualization techniques. In some embodiments, the annuloplasty prosthesis provides a radiographic, echogenic and/or other image enhanced image of a near entirety of the valve annulus.

17 Claims, 5 Drawing Sheets

U.S. PATENT DOCUMENTS

| | | | |
|---|---|---|---|
| 5,593,424 A | 1/1997 | Northrup, III | |
| 5,601,576 A | 2/1997 | Garrison | |
| 5,607,471 A | 3/1997 | Seguin et al. | |
| 5,617,397 A | 4/1997 | Jones et al. | |
| 5,669,919 A | 9/1997 | Sanders et al. | |
| 5,674,279 A | 10/1997 | Wright et al. | |
| 5,674,280 A | 10/1997 | Davidson et al. | |
| 5,683,402 A | 11/1997 | Cosgrove et al. | |
| 5,716,397 A | 2/1998 | Myers | |
| 5,824,066 A | 10/1998 | Gross | |
| 5,860,992 A | 1/1999 | Daniel et al. | |
| 5,972,030 A | 10/1999 | Garrison et al. | |
| 6,102,945 A | 8/2000 | Campbell | |
| 6,143,024 A | 11/2000 | Campbell et al. | |
| 6,159,240 A | 12/2000 | Sparer et al. | |
| 6,165,183 A | 12/2000 | Kuehn et al. | |
| 6,174,332 B1 | 1/2001 | Loch et al. | |
| 6,183,512 B1 | 2/2001 | Howance, Jr. et al. | |
| 6,187,040 B1 | 2/2001 | Wright | |
| 6,217,610 B1 | 4/2001 | Carpentier et al. | |
| 6,231,602 B1 | 5/2001 | Carpentier et al. | |
| 6,283,993 B1 | 9/2001 | Cosgrove et al. | |
| 6,319,280 B1 | 11/2001 | Schoon | |
| 6,368,348 B1 * | 4/2002 | Gabbay | 623/2.36 |
| 6,406,492 B1 | 6/2002 | Lytle | |
| 6,416,548 B2 | 7/2002 | Chinn et al. | |
| 6,416,549 B1 | 7/2002 | Chinn et al. | |
| 6,528,107 B2 | 3/2003 | Chinn et al. | |
| 6,565,603 B2 | 5/2003 | Cox | |
| 6,602,289 B1 | 8/2003 | Colvin et al. | |
| 6,695,866 B1 | 2/2004 | Kuehn et al. | |
| 6,726,717 B2 | 4/2004 | Alfieri et al. | |
| 6,749,630 B2 | 6/2004 | McCarthy et al. | |
| 6,786,924 B2 | 9/2004 | Ryan et al. | |
| 6,797,002 B2 | 9/2004 | Spence et al. | |
| 6,805,710 B2 | 10/2004 | Bolling et al. | |
| 6,858,039 B2 | 2/2005 | McCarthy | |
| 6,908,482 B2 | 6/2005 | McCarthy et al. | |
| 6,955,689 B2 | 10/2005 | Ryan et al. | |
| 2001/0010018 A1 | 7/2001 | Cosgrove et al. | |
| 2001/0021874 A1 | 9/2001 | Carpentier et al. | |
| 2001/0034551 A1 | 10/2001 | Cox | |
| 2001/0041933 A1 | 11/2001 | Thoma | |
| 2001/0049557 A1 | 12/2001 | Chin et al. | |
| 2001/0049558 A1 | 12/2001 | Liddicoat et al. | |
| 2002/0129820 A1 | 9/2002 | Ryan et al. | |
| 2002/0133180 A1 | 9/2002 | Ryan et al. | |
| 2002/0169503 A1 | 11/2002 | Lytle | |
| 2002/0173844 A1 | 11/2002 | Alfieri et al. | |
| 2003/0045929 A1 | 3/2003 | McCarthy et al. | |
| 2003/0093148 A1 | 5/2003 | Bolling et al. | |
| 2003/0125715 A1 | 7/2003 | Kuehn et al. | |
| 2004/0006384 A1 | 1/2004 | McCarthy | |
| 2004/0088047 A1 | 5/2004 | Spence et al. | |
| 2004/0167619 A1 * | 8/2004 | Case et al. | 623/1.34 |
| 2005/0004666 A1 | 1/2005 | Alfieri et al. | |
| 2005/0021135 A1 | 1/2005 | Ryan et al. | |
| 2005/0043791 A1 | 2/2005 | McCarthy et al. | |
| 2005/0049698 A1 | 3/2005 | Bolling et al. | |
| 2005/0131533 A1 | 6/2005 | Alfieri et al. | |
| 2005/0182487 A1 | 8/2005 | McCarthy et al. | |
| 2005/0192666 A1 | 9/2005 | McCarthy | |
| 2005/0246014 A1 | 11/2005 | McCarthy | |
| 2005/0256567 A1 | 11/2005 | Lim et al. | |
| 2005/0256568 A1 | 11/2005 | Lim et al. | |
| 2005/0256569 A1 | 11/2005 | Lim et al. | |
| 2005/0267572 A1 | 12/2005 | Schoon et al. | |
| 2006/0015179 A1 | 1/2006 | Bulman-Fleming et al. | |
| 2006/0025856 A1 | 2/2006 | Ryan et al. | |
| 2006/0129236 A1 | 6/2006 | McCarthy | |
| 2006/0217803 A1 | 9/2006 | Ingle et al. | |
| 2007/0078468 A1 | 4/2007 | Ryan et al. | |
| 2007/0078514 A1 | 4/2007 | Ryan et al. | |
| 2007/0100441 A1 | 5/2007 | Kron et al. | |
| 2007/0156234 A1 | 7/2007 | Adzich et al. | |
| 2007/0191939 A1 | 8/2007 | Ryan et al. | |
| 2007/0276478 A1 * | 11/2007 | Marmureanu et al. | 623/2.11 |
| 2007/0299513 A1 | 12/2007 | Ryan et al. | |

FOREIGN PATENT DOCUMENTS

| | | |
|---|---|---|
| EP | 0 338 994 | 10/1989 |
| EP | 0 495 417 | 7/1992 |
| EP | 1 034 753 | 2/2005 |
| WO | 91/17721 | 11/1991 |
| WO | 94/18909 | 9/1994 |
| WO | 99/04730 | 2/1999 |
| WO | 99/29269 | 6/1999 |
| WO | 99/49816 | 10/1999 |
| WO | 00/23007 | 4/2000 |
| WO | 00/59408 | 10/2000 |
| WO | 00/62715 | 10/2000 |
| WO | 00/74603 | 12/2000 |
| WO | WO 00/74603 | 12/2000 |
| WO | 01/87191 | 11/2001 |
| WO | 02/074197 | 9/2002 |
| WO | 03/020178 | 3/2003 |
| WO | 03/053289 | 7/2003 |
| WO | 2005/112830 | 12/2005 |

OTHER PUBLICATIONS

US 6,673,110, 1/2004, Alfieri et al. (withdrawn).
Ahmadi, A., et al., "Hemodynamic Changes Following Experimental Production and Correction of Acute Mitral Regurgitation With an Adjustable Ring Prosthesis," The Thoracic and Cardiovascular Surgeon, vol. 36, No. 6, pp. 313-319 (1988).
Alonso-Lei, "Adjustable Annuloplasty for Tricuspid Insufficiency," The Annals of Thoracic Surgery, (1988) 46(3), pp. 368-369.
Alonso-Lej, F., "The 'dynamic' mitral ring: A new concept in treating mitral insufficiency," Recent Progress in Mitral Valve Disease, pp. 45 and 443-449 (1984).
AnnuloFlex® and AnnuloFlo® Systems, Implantation techniques for mitral and tricuspid indications, CarboMedics (2003) (24 pages).
Belcher, J.R., "The Surgical Treatment of Mitral Regurgitation," British Heart Journal, vol. 26, pp. 513-523 (1964).
Bex J.P. and Lecompte Y., "Tricuspid valve repair using a flexible linear reducer," J. Cardiac Surg., 1:151 (1986).
Bolling, "Mitral Valve Reconstruction in the Patient with Heart Failure," Heart Failure Reviews, (2001) 6, pp. 177-185.
Bolling, S.F., "Mitral Reconstruction in Cardiomyopathy," The Journal of Heart Valve Disease, vol. 11, Suppl. 1, pp. S26-S31 (2002).
Bolling, S.F., et al., "Surgery for Acquired Heart Disease," The Journal of Thoracic and Cardiovascular Surgery, vol. 109, No. 4, pp. 676-683 (1995).
Bolling, et al., "Surgical Alternatives for Heart Failure," The Journal of Heart and Lung Transplantation, (2001) 20(7), pp. 729-733.
Carpentier, A., et al., "A New Reconstructive Operation for Correction of Mitral and Tricuspid Insufficiency," The Journal of Thoracic and Cardiovascular Surgery, vol. 61, No. 1, pp. 1-13 (1971).
Carpentier, A., "La Valvuloplastie Reconstitutive: Une Nouvelle Technique de Valvuloplastie Mitrale," Technique Chirugicale, No. 7, pp. 251-255 (1969).
Carpentier A., Deloche A., Hanania G., et al., "Surgical management of acquired tricuspid valve disease," J. Thorac. Cardiovasc. Surg., 67:53 (1974).
Carpentier, A.F., et al., "The 'Physio-Ring': An Advanced Concept in Mitral Valve Annuloplasty," Ann. Thorac. Surg., vol. 60, No. 5, pp. 1177-1186 (1995).
Carpentier-Edwards® Annuloplasty Rings (3 pages) (found in the file history of U.S. Appl. No. 10/918,503).
Carpentier-Edwards Physio™ Annuloplasty Ring (3 pages) (found in the file history for U.S. Appl. No. 10/918,503).
Castells, E., et al., "Long-Term Results with the Puig Massana-Shiley Annuloplasty Ring," The Journal of Cardiovascular Surgery, Abstracts, vol. 24, No. 4, p. 387 (1983).
Chachques, J.C., et al., "Absorbable Rings for Pediatric Valvuloplasty: Preliminary Study," Supplement IV to Circulation, vol. 82, No. 5, pp. IV-82-IV-88 (1990).
Cochran, et al., "Effect of Papillary Muscle Position on Mitral Valve Function: Relationship to Homografts," Ann. Thorac. Surg, (1998) 66:SS155-161.
Cooley, D.A., et al., "A Cost-Effective Dacron Annuloplasty Ring," The Annals of Thoracic Surgery, vol. 56, pp. 185-186 (1993).

Cooley, D.A., "Ischemic Mitral Insufficiency," Cardiac Surgery: State of the Art Reviews, vol. 6, No. 2, pp. 237-249 (1992).
Cooley, D.A., et al., "Mitral Leaflet Prolapse: Surgical Treatment using a Posterior Annular Collar Prosthesis," Cardiovascular Diseases Bulletin of the Texas Heart Institute, vol. 3, No. 4, pp. 438-443 (1976).
Cosgrove, D.M., III, et al., "Initial Experience with the Cosgrove-Edwards Annuloplasty System," The Annals of Thoracic Surgery, vol. 60, pp. 499-504 (1995).
Dagum et al., "Three-dimensional geometric comparison of partial and complete flexible mitral annuplasty rings," The J. of Thorac. and Cardiovasc. Surg., vol. 122, No. 4 (2001).
Deloche, A., et al., "Valve Repair with Carpentier Techniques," The Journal of thoracic and Cardiovascular Surgery, vol. 99, No. 6, pp. 990-1002 (1990).
Department of Health & Human Services letter and attachments regarding file K926138, Carpentier-Edwards Physio™ Annuloplasty Ring, Model 4450 Mitral, dated Jun. 22, 1993 (295 pages).
Duran, C.G., et al., "Clinical and Hemodynamic Performance of a Totally Flexible Prosthetic Ring for Atrioventricular Valve Reconstruction," The Annals of Thoracic Surgery, vol. 22, No. 5, pp. 458-463 (1976).
Duran, C.G., "Reconstructive procedures of the Mitral Valve Including Ring Annuloplasty," Modern Technics in Surgery, 20 (1979).
Duran, C.G., et al., "Stability of Mitral Reconstructive Surgery at 10-12 Years for Predominantly Rheumatic Valvular Disease," Circulation Supplement I, vol. 78, No. 3, pp. I-91-I-96 (1988).
Durán, C.M.G., et al., "A New Absorbable Annuloplasty Ring in the Tricuspid Position: An Experimental Study," The Thoracic and Cardiovascular Surgeon, vol. 34, No. 6, pp. 377-379 (1986).
Duran, C.,M.G., et al., "Valve Repair in Rheumatic Mitral Disease," Supplement to Circulation, vol. 84, No. 5, pp. III 125-III 132 (1990).
Erk, M.K., "Morphological and Functional Reconstruction of the Mitral Valve: A New Annuloplastic Procedure," Texas Heart Institute Journal, vol. 9, pp. 329-334 (1982).
Erk, M.K., et al., "Semi-frame Mitral Annuloplasty," Cardiac Reconstructions pp. 157-163 (1989).
Flachskampf, et al., "Analysis of Shape and Motion of the Mitral Annulus in Subjects With and Without Cardiomyopathy by Echocardiographic 3-Dimensional Reconstruction," Journal of the American Society of Echocardiography, (2000) 13(4), pp. 277-287.
Freed, et al., "Prevalence and Clinical Outcome of Mitral-Valve Prolapse," The New England Journal of Medicine, (1999) 341(1), pp. 1-7.
Fundarò, P., et al., "Polytetrafluoroethylene Posterior Annuloplasty for Mitral Regurgitation," The Annals of Thoracic Surgery, Correspondence, vol. 50, No. 1, pp. 165-166 (1990).
Galler M. Kronzon I, Slater J., et al., "Long-term follow-up after mitral valve reconstruction: incidence of post-operative left ventricular out flow obstruction," Circulation, 74:I-99 (1986).
Gatti, et al., "Preliminary experience in mitral valve repair using the Cosgrove-Edwards annuloplasty ring," Interact Cardiovasc Thorac Surg, (2003) 2:256-261.
Ghosh, P.K., "Mitral Annuloplasty: A Right-Side View," The Journal of Heart Valve Disease, vol. 5, pp. 286-293 (1996).
Gorman, et al., "Dynamic Three-Dimensional Imaging of the Mitral Valve and Left Ventricle by Rapid Sonomicrometry Array Localization," J Thorac Card Surg, 112(3), (1996) pp. 712-726.
Gorman, et al., "The Effect of Regional Ischemia on Mitral Valve Annular Saddle Shape," Ann Thorac Surg (2004) 77, pp. 544-548.
Gorton, M.E., et al., "Mitral Valve Repair Using a Flexible and Adjustable Annuloplasty Ring," The Annals of Thoracic Surgery, vol. 55, pp. 860-863 (1993).
Gregori, F., et al., "Mitral Valvuloplasty with a New Prosthetic Ring," Official Journal of the European Association for Cardio-thoracic Surgery, vol. 8, No. 4, pp. 168-172 (1994).
Gregori, F., Jr., et al., "Um Novo Modelo De Anel Protetico Para Pacientes Com Insuficiencia Valvar Mitral. Relato de Dois Casos," Arquivos Brasileiros de Cardiologia, vol. 50, No. 6, pp. 417-420 (1988).
Haverich, et al., "Experimental and Clinical Experiences with Double-velour Woven Dacron Prostheses," Thorac. Cardiovasc. Surgeon 34 (1986) pp. 52-53.
Hendren, W.G., et al., "Mitral Valve Repair for Ischemic Mitral Insufficiency," The Annals of Thoracic Surgery, vol. 52, pp. 1246-1252 (1991).
Henze, A., et al., "The Adjustable Half-Moon: An Alternative Device for Tricuspid Valve Annuloplasty," Scandinavian Journal of Thoracic and Cardiovascular Surgery, vol. 18, pp. 29-32 (1984).
Jimenez, et al., "Effects of a Saddle Shaped Annulus on Mitral Valve Function and Chordal Force Distribution: An in Vitro Study," Annals of Biomedical Engineering, (2003) vol. 31, pp. 1171-1181.
Kasegawa, H., et al., "Physiologic Remodeling Annuloplasty to Retain the Shape of the Anterior Leaflet: A New Concept in Mitral Valve Repair," The Journal of Heart Valve Disease, vol. 6, pp. 604-607 (1997).
Katz, N.M., "Current Surgical Treatment of Valvular Heart Disease," American Family Physician, vol. 52, No. 2, pp. 559-568 (1995).
Kaye, D.M., et al., "Feasibility and Short-Term Efficacy of Percutaneous Mitral Annular Reduction for the Therapy of Heart Failure—Induced Mitral Regurgitation," Circulation, Brief Rapid Communication, No. 108, pp. 1795-1797 (2003).
Kurosawa, H., et al., "Mitral Valve Repair by Carpentier-Edwards Physio Annuloplasty Ring," The Japanese Journal of Thoracic and Cardiovascular Surgery, vol. 47, pp. 355-360 (1999).
Lachmann, J., M.D., et al., "Mitral Ring Annuloplasty: An Incomplete Correction of Functional Mitral Regurgitation Associated with Left Ventricular Remodeling," Current Cardiology Reports, vol. 3, pp. 241-246 (2001).
Levin et al., "Three-Dimensional Echocardiographic Reconstruction of the Mitral Valve, With Implications for the Diagnosis of Mitral Valve Prolapse," Circulation, 1989; 80(3):589-598.
Levine, R.A., et al., "The Relationship of Mitral Annular Shape to the Diagnosis of Mitral Valve Prolapse," Circulation, vol. 75, No. 4, pp. 756-767 (1987).
Martin, S.L., et al., "Echocardiographic Evaluation of Annuloplasty Rings: Comparison of Continuity Equation and Pressure Half-Time Methods," Journal of The American Society of Echocardiography, vol. 5, No. 3, p. 322 (1992).
Medtronic® Sculptor™ Annuloplasty Ring brochure, Medtronic Inc. (1993) (6 pages).
Melo, et al., "Atrioventricular Valve Repair Using Externally Adjustable Flexible Rings," The Journal of Thoracic and Cardiovascular Surgery, (1995) 110(5), pp. 1333-1337.
Melo, J.Q., et al., "Surgery for Acquired Heart Disease: Atrioventricular Valve Repair using Externally Adjustable Flexible Rings," The Journal of Thoracic and Cardiovascular Surgery, No. 110, pp. 1333-1337 (1995).
Miller, "Ischemic mitral regurgitation redux—To repair or to replace?" The Journal of Thoracic and Cardiovascular Surgery, (2001) 122(6), pp. 1059-1062.
Morse, D., et al., "Cardiac Valve Identification Atlas and Guide," Chapter 10 in Guide to Prosthetic Cardiac Valves, edited by Dryden Morse, Robert M. Steiner, and Javier Fernandez, Springer-Verlag New York Inc. (1985).
Murphy, J.P., et al., "The Puig-Massana-Shiley Annuloplasty Ring for Mitral Valve Repair: Experience in 126 Patients," The Annals of Thoracic Surgery, vol. 43, pp. 52-58 (1987).
Ogus, T.N., et al., "Posterior Mitral Annuloplasty with an Adjustable Homemade Ring," Journal of Cardiac Surgery, vol. 17, No. 3, pp. 226-228 (2002).
Pellegrini, A., et al., "Posterior Annuloplasty in the Surgical Treatment of Mitral Insufficiency," The Journal of Heart Valve Disease, vol. 2, pp. 633-638 (1993).
Reece, I.J., et al., "Surgical Treatment of Mitral Systolic Click Syndrome: Results in 37 Patients," The Annals of Thoracic Surgery, vol. 39, No. 2, pp. 155-158 (1985).
Rubenstein, F., et al., "Alternatives in Selection of Rings for Mitral Annuloplasty," Current Opinion in Cardiology, vol. 16, No. 2, pp. 136-139 (2001).
Salati, M., et al., "Annular Remodeling with Pericardial Reinforcement: Surgical Technique and Early Results," The Journal of Heart Valve Disease, vol. 2, pp. 639-641 (1993).
Salati, M., et al., "Posterior Pericardial Annuloplasty: A Physiocological Correction?", European Journal of Cardio-Thoracic Surgery, vol. 5, pp. 226-229 (1991).

Salvador, L., et al., "The Pericardium Reinforced Suture Annuloplasty: Another Tool Available for Mitral Annulus Repair," Journal of Cardiac Surgery, vol. 8, pp. 79-84 (1993).

Sato, et al., "The Biologic Fate of Dacron Double Velour Vascular Prostheses—A Clinicopathological Study," Japanese Journal of Surgery, (1989) 19(3), pp. 301-311.

Seguin, et al., "Advance in Mitral Valve Repair Using a Device Flexible in Three Dimensions," ASAIO Journal (1996), 42:M368-M371.

Shumway, S.J., et al., "A 'Designer' Annuloplasty Ring for Patients with Massive Mitral Annular Dilation," The Annals of Thoracic Surgery, vol. 46, No. 6, pp. 695-696 (1988).

Smolens, I., et al., "Current Status of Mitral Valve Reconstruction in Patients with Dilated Cardiomyopathy," Ital. Heart J., vol. 1, No. 8, pp. 517-520 (2000).

Smolens, et al., "Mitral valve repair in heart failure," The European Journal of Heart Failure, (2000) 365-371.

Tsakiris, A.G., "The psysiology of the mitral valve annulus," in The Mitral Valve-apluridisciplinary Approach, ed Kalmanson D. Publishing Sciences Group, Acton, Mass., p. 21 (1976).

Victor, S., et al., "Truly Flexible D-Shaped Autogenous Pericardial Ring for Mitral Annuloplasty," The Annals of Thoracic Surgery, vol. 56, pp. 179-180 (1993).

Vongpatanasin, W., et al., "Prosthetic Heart Valves," The New England Journal of Medicine, vol. 335, No. 6, pp. 407-416 (1996).

Parish, et al., "The Dynamic Anterior Mitral Annulus," The Society of Thoracic Surgeons, (2004) pp. 1248-1255.

Timek, et al., "Annular Height-to-Commissural Width Ratio of Annuloplasty Rings In Vivo," Circulation, (2005); 112[suppl I]:I-423-I-428.

Glasson, et al., Three-Dimensional Regional Dynamics of the Normal Mitral Annulus During Left Ventricular Ejection, Journal of Thoracic and Cardiovascular Surgery, vol. 111, No. 3, (1996), pp. 574-585.

Glasson, et al., "Three-Dimensional Dynamics of the Canine Mitral Annulus During Ischemic Mitral Regurgitation," Society of Thoracic Surgeons, (1996), pp. 1059-1068.

Tibayan, et al., "Annular Remodeling in Chronic Ischemic Mitral Regurgitation: Ring Selection Implications," Society of Thoracic Surgeons, (2003), pp. 1549-1555.

Hasenkam, et al., "What force can the myocardium generate on a prosthetic mitral valve ring? An animal experimental study," Journal of Heart Valve Dis. (1994), 1 pg., found on website: http://www.ncbi.nlm.nih.gov/sites/entrez?cmd=Retrieve&db=PubMed&list_uids=8087273&dopt=Citation.

St. Jude Medical® Rigid Saddle Ring with EZ Suture™ Cuff, 4 pgs., printed Sep. 2007, found on website: http://www.sjm.com/devices/device.aspx?name=St.+Jude+Medical%26%23174%3B+Rigid+Saddle+Ring+with+EZ+Suture%26%23153%3B+Cuff&location=us&type=23.

Salgo, et al., "Effect of Annular Shape on Leaflet Curvature in Reducing Mitral Leaflet Stress," Circulation, (2002); 106:711-717.

Co-pending U.S. Appl. No. 11/809,194, filed May 31, 2007, entitled "Annuloplasty Ring and Method," in the name of Timothy R. Ryan et al.

Lawrence, et al., "A Biomechanical Analysis of Suture Materials and Their Influence on a Four-Strand Flexor Tendon Repair," The Journal of Hand Surgery, vol. 30, No. 4, 2005, pp. 836-841.

* cited by examiner

ANNULOPLASTY PROSTHESIS WITH IN VIVO SHAPE IDENTIFICATION AND RELATED METHODS OF USE

PRIORITY CLAIM

This application claims the benefit of U.S. Provisional Patent Application having Ser. No. 60/810,599, filed on Jun. 2, 2006, entitled "ANNULOPLASTY PROSTHESIS WITH IN VIVO SHAPE IDENTIFICATION AND RELATED METHODS OF USE," the entire disclosure of which is incorporated herein by reference for all purposes.

BACKGROUND

The present invention relates generally to devices and methods for repair of heart valves, such as annuloplasty rings and bands. More particularly, it relates to annuloplasty prostheses providing non-invasive valve status information following implant.

Annuloplasty prostheses, generally categorized as either annuloplasty rings or annuloplasty bands, are employed in conjunction with valvular reconstructive surgery to assist in the correction of heart valve defects such as stenosis and valvular insufficiency. There are two atrio-ventricular valves in the heart. The mitral valve is located on the left side of the heart, and the tricuspid valve located on the right side. Anatomically speaking, each valve type forms or defines a valve annulus and valve leaflets. To this end, the mitral and tricuspid valves differ significantly in anatomy. For example, the annulus of the mitral valve is somewhat "D" shaped, whereas the tricuspid valve annulus is more nearly circular.

Both valves can be subjected to or incur damage that requires the valve in question to be repaired or replaced. The effects of valvular dysfunction vary. For example, mitral regurgitation, a complication of end-stage cardiomyopathy, has more severe physiological consequences to a patient as compared to tricuspid valve regurgitation. Regardless, many of the defects are associated with dilatation of a valve annulus. This dilatation not only prevents competence of a valve, but also results in distortion of the normal shape of a valve orifice. Remodeling of an annulus is therefore central to most reconstructive procedures on a mitral valve. In this regard, clinical experience has shown that repair of a valve, when technically possible, produces better long-term results as compared to valve replacement.

Many procedures have been described to correct the pathology of the valve leaflets and their associated chordae tendinae and papillary muscles. For example, with respect to the mitral valve, it is a bicuspid valve having a large posterior leaflet that coapts or meets with a smaller anterior leaflet. The part of the mitral valve annulus that is attached to the anterior leaflet is called the anterior aspect, while the part attached to the posterior leaflet is called the posterior aspect. There are two fibrous trigones that nearly straddle the anterior aspect. With this in mind, in mitral repairs, it is considered important to preserve the normal distance between the two trigones. A significant surgical diminution of the inter-trigonal distance may cause left ventricular outflow obstruction. Thus, it is desirable to maintain the natural inter-trigonal distance during and following mitral valve repair surgery.

Consequently, when a mitral valve is repaired surgically, the result is generally a reduction of the size of the posterior aspect of the mitral valve annulus. As part of a typical mitral valve repair, an annulus or segment thereof (e.g., anterior or posterior aspect) is diminished (i.e., constricted) so that the leaflets may coapt correctly upon closing of the valve, or an annulus is stabilized to prevent post-operative dilatation from occurring, either as frequently achieved by implantation of a prosthetic ring or band in a supra annular position. The purpose of a ring or band is to restrict and/or support an annulus to correct and/or prevent valvular insufficiency. However, it is important not to overly restrict an annulus as an unacceptable valvular stenosis may result. In tricuspid valve repair, constriction of an annulus usually takes place by positioning a band partially about the posterior leaflet segment and a small portion of the adjacent anterior leaflet segment. The septal leaflet segment is not usually required to be shortened.

As described above, both annuloplasty rings and annuloplasty bands are available for repair of an atrio-ventricular valve. Examples of annuloplasty rings are shown in U.S. Pat. Nos. 5,306,296; 5,669,919; 5,716,397; and 6,159,240, the teachings of which are incorporated herein by reference. In general terms, annuloplasty rings completely encompass both the anterior and posterior aspects of a valve annulus, and have either a rigid (or semi-rigid) design, or a flexible design. Annuloplasty bands, on the other hand, are specifically designed to primarily encompass only a portion of the valve annulus. With the rigid or semi-rigid configuration, an annuloplasty ring serves to remodel the dysfunctional valve annulus to a desired shape such as that which would mimic the normal systolic shape of the valve. In this regard, and relative to the mitral valve, recent studies have identified that the healthy mitral valve annulus has a natural saddle shape that becomes exaggerated in systole. Efforts have been made to provide a rigid annuloplasty ring that more closely mimics this saddle shape, for example as shown in U.S. Pat. No. 6,858,039 and U.S. Publication No. 2003/0093148, the teachings of which are incorporated herein by reference. While viable, this remodeling/rigid annulus support may overtly restrict natural movement of the mitral valve annulus when functioning during diastole and systole, especially in the mitral valve anterior aspect as suggested by Parrish, L. M., et al., *The Dynamic Anterior Mitral Annulus*, (Annals. of Thoracic Surgery 2004; 78:1248-55). Further, once implanted, these and other conventional annuloplasty prosthesis do not provide a means for post-operative evaluation or monitoring of a shape of a repaired valve annulus.

Annuloplasty bands have been developed as an alternative to an annuloplasty ring. An annuloplasty band can have a rigid (or semi-rigid) design, or can be flexible. With the rigid or semi-rigid approach, an annuloplasty band serves to remodel a portion of a valve annulus, whereas other portions of a valve annulus to which an annuloplasty band is not applied are free to move or function in a more natural manner. Thus, for example, with respect to a mitral valve annulus, an annuloplasty band is implanted at the posterior aspect of the annulus; a majority or all of the anterior aspect is unencumbered by the annuloplasty band, and thus can function or move in a more natural manner. Examples of annuloplasty band designs are described in U.S. Pat. No. 6,786,924, as well as U.S. Pat. No. 5,824,066 and PCT International Patent Publication No. WO00/74603, the teachings of all of which are incorporated herein by reference. While highly viable, conventional annuloplasty band configurations again do not provide a surgeon with the ability to easily review a complete shape of the valve annulus or otherwise provide a subsequent indication that an annuloplasty band has been implanted (as opposed to an annuloplasty ring).

In light of the above, a need exists for annuloplasty prosthesis providing a more complete representation of the repaired valve annulus via non-invasive, post-operative procedures.

SUMMARY

Aspects in accordance with principles of the present invention relate to an annuloplasty prosthesis for repairing an atrio-ventricular valve having a valve annulus. The annuloplasty prosthesis includes a sheath, an arcuate stiffening element, and an imaging element that may comprise a radiographic, echogenic and/or other imaging enhancing material. The arcuate stiffening element is disposed within the sheath and defines discrete, first and second ends separated by a lateral spacing. The imaging element is disposed within the sheath along the lateral spacing. With this configuration, following implant to the valve annulus, the imaging element provides a mechanism for non-invasively evaluating a shape of the valve annulus, for example via radiographic visualization techniques. In some embodiments, the stiffening element is also formed of a radiopaque, echogenic and/or other image enhancing material. With these embodiments, the annuloplasty prosthesis can provide a radiographic representation of an entirety or a near entirety of the valve annulus. In yet other embodiments, the imaging element is a barium sulfate-impregnated strip. In other embodiments in accordance with principles of the present invention, the annuloplasty prosthesis is adapted for repairing a mitral valve annulus, with a segment of the prosthesis otherwise corresponding with the imaging element adapted for implantation to an anterior aspect of the mitral valve annulus.

Other aspects in accordance with principles of the present invention relate to a method of implanting an annuloplasty prosthesis to an annulus of a heart valve of a patient. The method includes providing an annuloplasty prosthesis including a sheath, an arcuate stiffening element, and an imaging element. The stiffening element is disposed within the sheath and defines discrete, first and second ends separated by a lateral spacing. The imaging element is disposed within the sheath along the lateral spacing. With this in mind, the annuloplasty prosthesis is implanted to the valve annulus. A radiographic, echogenic and/or other image enhanced image of the valve annulus is generated, including a radiographic, echogenic and/or other image enhanced image of the imaging element. Finally, a status of the valve is evaluated based upon the radiographic, echogenic and/or other image enhanced image. In some embodiments, the evaluated status of the valve relates to a flexibility of the valve annulus. In other embodiments, the generated radiographic, echogenic and/or other image enhanced image further includes an image of the stiffening element, with the evaluated status relating to a calculated orifice area of the valve annulus.

DETAILED DESCRIPTION

Figure 1:
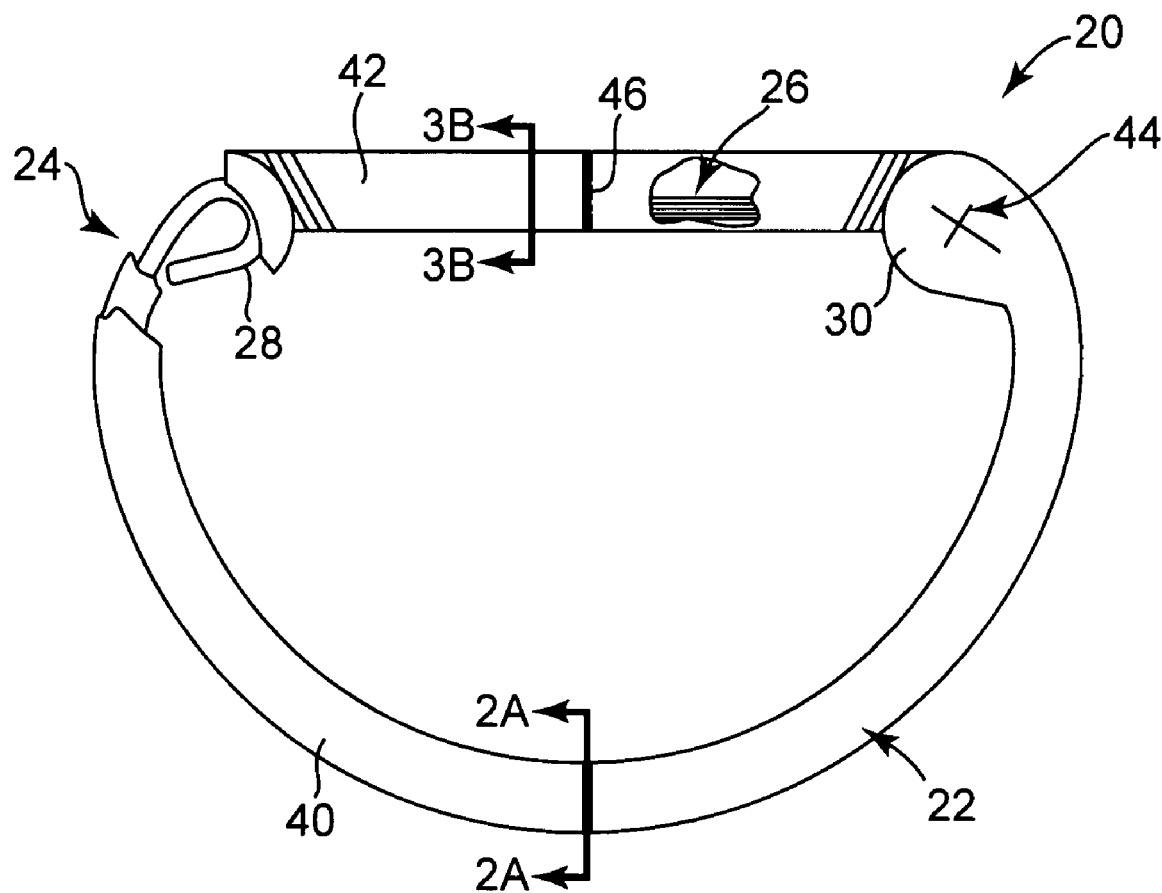
FIG. 1 is a top view of an annuloplasty prosthesis in accordance with principles of the present invention, with portions peeled away.

An annuloplasty prosthesis 20 in accordance with principles of the present invention is illustrated in FIG. 1. The annuloplasty prosthesis 20 is particularly adapted to repair one of the atrio-ventricular valves, such as the mitral or tricuspid valves. As a point of reference, the annuloplasty prosthesis 20 illustrated in FIG. 1 is configured for mitral valve annulus repair, it being understood that other shapes may be incorporated for other valve annulus anatomies (e.g., the tricuspid valve annulus). Thus, the present invention is not limited to mitral valve annuloplasty.

The annuloplasty prosthesis 20 generally includes a fabric sheath 22, an arcuate stiffening element 24, and an imaging element 26. Details on the various components are provided below. In general terms, however, the stiffening element 24 and the imaging element 26 are disposed within the sheath 22, with at least the stiffening element 24 exhibiting sufficient structural rigidity to effectuate desired valve annulus remodeling. To this end, the stiffening element 24 extends between discrete, first and second ends 28, 30 (the second 30 being referenced generally in FIG. 1). Although not necessary for practice of the present invention, other functional elements can be incorporated between the ends 28, 30. In this regard, co-pending United States Patent Application, entitled ANNULOPLASTY RING AND METHOD, and Ser. No. 11/809,194, and filed on even date, is incorporated by reference in its entirety. The imaging element 26 extends along a lateral spacing between the first and second ends 28, 30 and provides a radiographic, echogenic or otherwise image enhanced imagable body following implant. As a point of reference, the above-described construction forms the annuloplasty prosthesis 20 to define a first segment 40 and a second segment 42. The first segment 40 corresponds with a region of the stiffening element 24, whereas the second segment 42 corresponds with a region of the imaging element 26.

The imaging element 26 may be radiopaque, echogenic and/or otherwise image enhanced so that it may readily be visualized after implantation using various existing techniques or any future developed techniques, including x-ray, MRI, echogram, etc. Any energy technologies that are known or developed that work similarly may be used. By "radiopaque," it is meant that the material or element prevents the passage of radiation. "Radiation" is meant to include electromagnetic energy, light, etc. By "echogenic," it is meant that it reflects sound waves. By "image enhancement," it is meant that a material is utilized that is directly related to the ability to more clearly discern the material based upon the type of energy that is used for imaging purposes.

In some embodiments, the annuloplasty prosthesis 20 is akin to the annuloplasty prostheses described in U.S. Pat. No. 6,786,924, although other configurations are also contemplated. With this in mind, the sheath 22 comprises a knitted, polyester (e.g., Dacron™) fabric in some embodiments, although woven, non-woven (e.g., spun-bond, melt-blown, staple fiber matrix, etc.) or braided fabrics are also acceptable, as well as sheaths formed of harvested biological tissue (e.g., pericardial tissue). While the sheath 22 is illustrated as being provided as a single, continuous body, in other embodiments, the sheath 22 can be formed from two or more separately-provided sections. For example, a first sheath section can be employed for the first segment 40, and a second sheath section can be provided for the second segment 42. Various indicia can be formed on the sheath 22, for example end markers 44. In some embodiments, a suture marker 46 is applied to an exterior of the sheath 22 along the second segment 40, for example at an approximate center thereof, to assist in properly orienting the prosthesis 20 during implant.

Figure 2A:
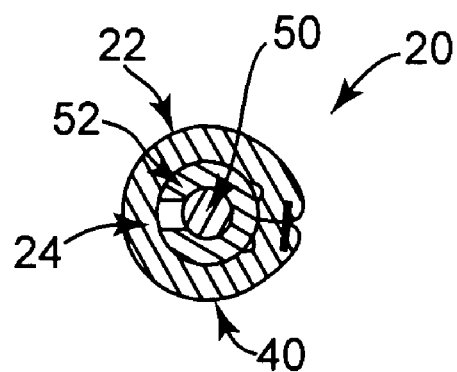
FIG. 2A is a cross-sectional view of the annuloplasty prosthesis of FIG. 1 along the lines 2A-2A.

The stiffening element 24 is generally arcuate in shape, extending from the first end 28 to the second end 30. With additional reference to FIG. 2A, in some embodiments the stiffening element 24 or comprises a stiffening wire 50 along with a protective coating 52 encompassing a portion of a length of the wire 50. For example, the protective coating 52 can be a biocompatible, biostable, implantable, medical grade elastomeric material such as elastomeric thermoplastic polymers (e.g., polyurethane) or silicone (e.g., liquid silicone rubber (LSR)). Alternatively, the protective coating 52 can be provided as a tubing of appropriate material placed over the wire 50. In yet other embodiments, the protective coating 52 can be eliminated.

As alluded to above, the stiffening element 24, and in particular the stiffening wire 50, is characterized as exhibiting sufficient rigidity for forcing or remodeling a valve annulus to a desired shape (i.e., conforming with the shape of the stiffening element 24). With this in mind, in some embodiments the stiffening element 24 is shaped to match a native or natural shape of a valve annulus to which the annuloplasty prosthesis 20 is to be applied. Thus, the stiffening element 24 can be generally shaped to mimic a native natural mitral valve annulus anatomy (i.e., generally symmetrical horseshoe-like shape) for mitral valve annulus repair; can be generally shaped to mimic a native natural tricuspid valve annulus anatomy (i.e., non-symmetrical offset curve) for tricuspid valve annulus repair; etc.

Figure 2B:
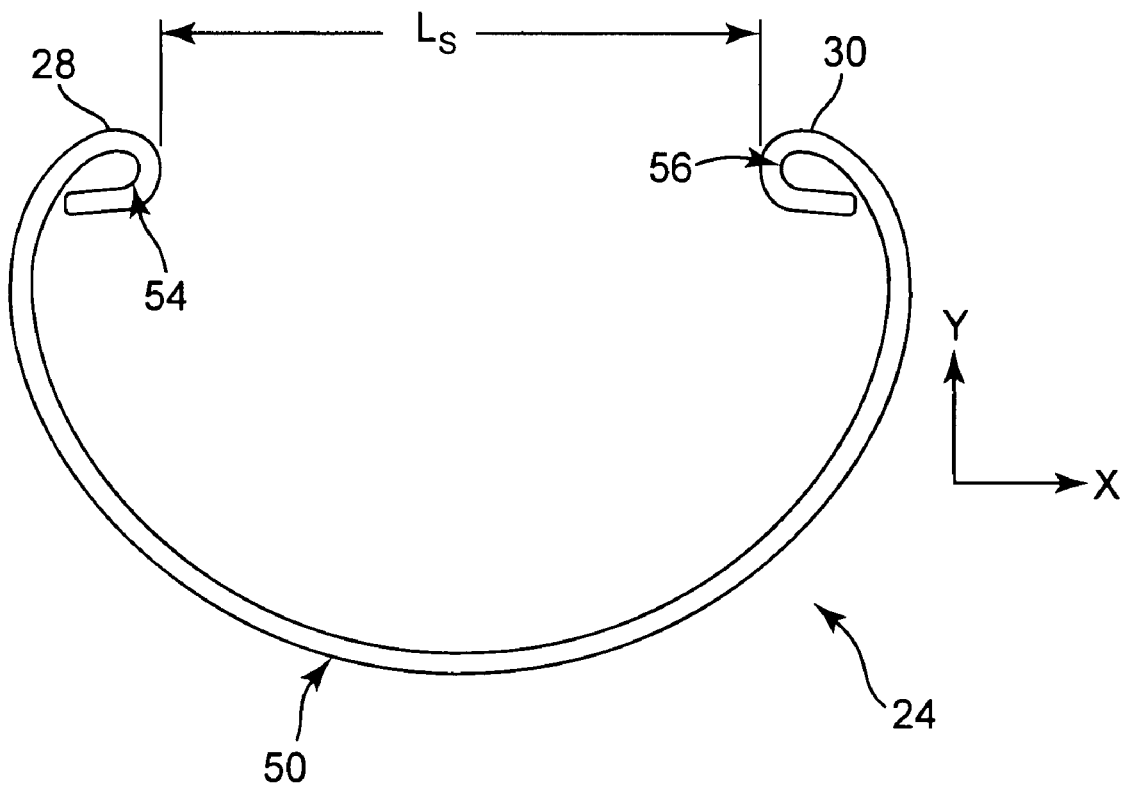
FIG. 2B is a top view of a stiffening element employed in the annuloplasty prosthesis of FIG. 1.
Figure 2C:
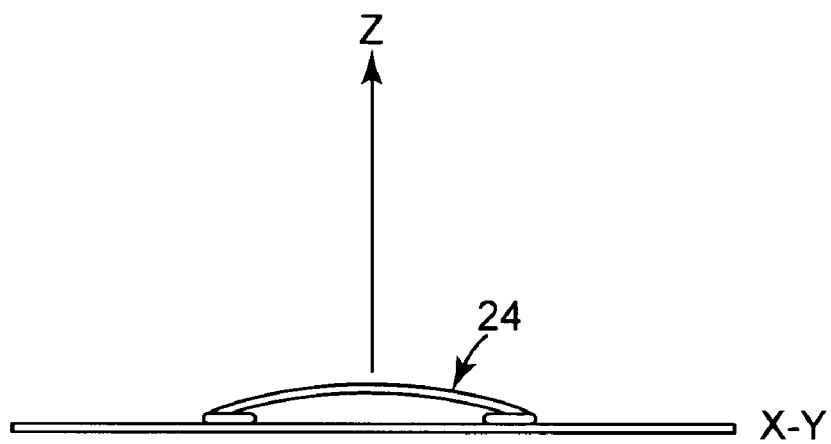
FIG. 2C is a side view of the stiffening element of FIG. 2B in an X, Y plane and Z direction, illustrating a saddle-shaped curve.

For example, in some embodiments, the stiffening element 24 defines a compound curve in the X-Y plane (as shown in FIG. 2B) and as described in U.S. Pat. No. 6,786,924. Further, and with additional reference to FIG. 2C, the stiffening element 24 can be generally saddle-shaped in the Z direction. In this regard, the level or severity of the saddle shape can be selected as desired. In some embodiments, for example, a saddle shape defined by the stiffening element 24 approximates the variations in height evidenced or experienced by the posterior aspect of a healthy mitral valve annulus in a systolic state or a diastolic state as described, for example, in Thomasz, A. T., et al., *Annular Height-to-Commissural Width Ratio of Annuloplasty Rings In Vivo*, (Circulation, 2005; 112 ([Suppl. I]:I-423-428), the teachings of which are incorporated herein by reference. Alternatively, the stiffening element 24 can be substantially planar in the Z direction. Regardless, and as best shown in FIG. 2B, a lateral spacing $L_S$ is established between the discrete ends 28, 30 of the stiffening element 24.

The stiffening element 24 is configured, in some embodiments, to form or include eyelets 54, 56 at the first and second ends 28, 30, respectively. For example, where the stiffening element 24 includes the wire 50, the wire 50 can be bent back onto itself at the opposing ends 28, 30 to form the eyelets 54, 56. In other embodiments, the eyelets 54, 56 can be eliminated.

Regardless of the exact shape defined by the stiffening element 24, in some embodiments, the stiffening element 24 can be provided with a radiopaque and/or echogenic characteristic so that it may be readily visualized after implantation. For example, the wire 50 can be formed of a radiopaque metal, and in particular, a biocompatible metal, such as an MP35N alloy, Elgiloy™ Co—Cr—Ni alloy wire (from American Gauge & Machine Company, Elgin, Ill.), Haynes™ alloy (Haynes International, Inc., of Kokomo, Ind.), titanium, stainless steel, shape memory material such as Nitinol™, etc. For example, suitable wire for the stiffening element wire 50 is the wrought cobalt-35, nickel-20, chromium-10, molybdenum alloy identified as "MP35N", available from Carpenter Technology Corp., of Wyomissing, Pa., although other materials are also acceptable. In other embodiments, the stiffening element 24 can comprise a molded polymeric element. In this alternative embodiment, the molded polymeric element preferably includes a radiopaque filler, such as, but not limited to, barium sulfate. With this approach, the eyelets 54, 56 can be integrally molded with a remainder of the stiffening element 24.

Figure 3A:
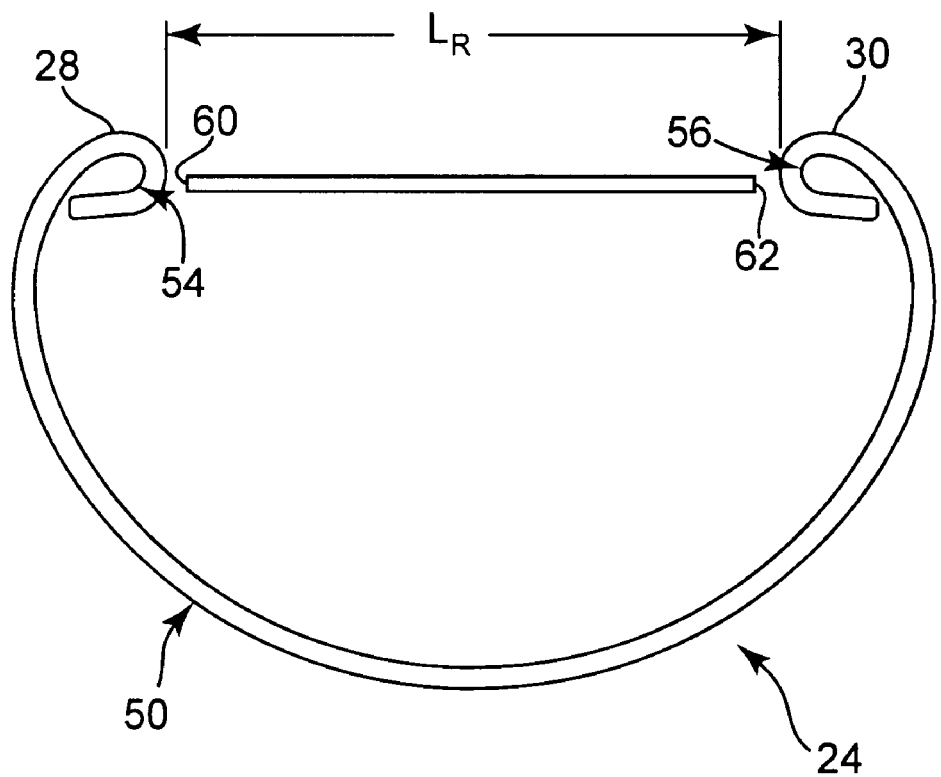
FIG. 3A is a top view of an imaging element employed in the annuloplasty prosthesis of FIG. 1, along with the stiffening element of FIG. 2B.

Returning to FIG. 1, the imaging element 26 is illustrated as disposed within the sheath 22 and extends along or between the lateral spacing $L_S$ (FIG. 2B) established between the first and second ends 28, 30 of the stiffening element 24. For example, and with additional reference to FIG. 3A that otherwise illustrates the stiffening element 24 and the imaging element 26 apart from the sheath 22, the imaging element 26 is an elongated body having a length $L_R$ that approximates a length of the lateral spacing $L_S$ between the first and second ends 28, 30 (when the stiffening element 24 is otherwise in a natural state). In this regard, the imaging element 26 defines a first end 60 and a second end 62. With these conventions in mind, in some embodiments, the length $L_R$ of the imaging element 26 is slightly less than the lateral spacing $L_S$ between the first and second ends 28, 30 of the stiffening element 24 such that upon final assembly, a slight gap exists between the first end 60 of the imaging element 26 and the first end 28 of the stiffening element 24; similarly, a slight gap exists between the second end 62 of the imaging element 26 and the second end 30 of the stiffening element 24. Alternatively, the imaging element 26 can be secured to one or both of the first and second ends 60, 62 of the stiffening element 24. Conversely, the imaging element 26 can have a length $L_R$ shorter than that depicted in FIG. 3A, but preferably has a length $L_R$ that is at least 50% of a length of the lateral spacing $L_S$.

The benefit of extending the imaging element 26 between the ends 28, 30 is that the image of an anterior aspect of an annulus is complete. However, less of the length between the ends 28, 30 is still effective to show at least a portion of the anterior aspect.

There is no need for the imaging element 26 to be strip-like. The imaging element 26 can be varied side to side or end to end. Alternatively it can be an element of any shape suspended or operatively positioned between the ends 28, 30 or attached to one of the ends 28, 30.

In addition to the length characteristics described above, in some embodiments, the imaging element 26 has a width approximating, preferably greater than, a diameter of the stiffening element wire 50. As described in greater detail below, this one embodiment enhances radiographic visualization of the annuloplasty prosthesis 20 as a whole. Alternatively, however, the imaging element 26 can have other widths that are less than that of the stiffening element wire 50.

Figure 3B:
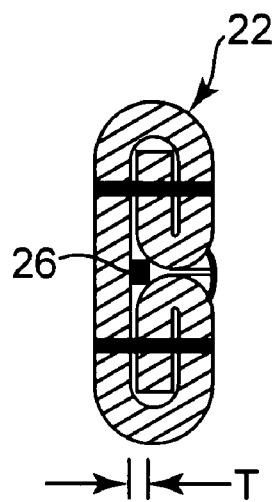
FIG. 3B is a cross-sectional view of the annuloplasty prosthesis of FIG. 1 along the lines 3B-3B.

In addition to the above-described width attributes, in some embodiments the imaging element 26 is thin relative to the thickness of the stiffening element wire 50 so as to not overtly affect a desired low profile attribute of the annuloplasty prosthesis 20. The imaging element 26 can be much less thick since an image is typically done in two dimensions from a substantially perpendicular direction. For example, and with reference to FIG. 3B, in some embodiments the imaging element 26 has a thickness T of not more than 0.8 mm, more preferably not more than about 0.6 mm. With this construction, and in connection with the one embodiment of the sheath 22 shown in FIG. 3B in which the sheath 22 is folded upon itself to capture the imaging element 26, the second segment 42 (best shown in FIG. 1) of the annuloplasty prosthesis 20 has a low profile attribute characterized by a maximum cross-sectional thickness of no greater than about 3 mm, more preferably no greater than about 2.7 mm, even more preferably no greater than about 2.5 mm. While other thicknesses are also acceptable (e.g., greater than 3 mm), this low profile attribute of the second segment 42 is commensurate with a low profile configuration of the first segment 40 (FIG. 1), best characterized with reference to FIG. 2A in which a maximum cross-sectional thickness of the annuloplasty prosthesis 20 along the first region 40 is not greater than about 3 mm, more preferably no greater than about 2.7 mm, even more preferably no greater than about 2.5 mm. Once again, however, other dimensions are also envisioned.

In some embodiments, the imaging element 26 has a flexible construction, for example characterized as being more flexible than the stiffening element 24, and in particular the stiffening element wire 50. With this configuration, the imaging element 26, and thus the second segment 42 of the annuloplasty prosthesis 20 (FIG. 1), can readily "move" with movement of the valve annulus to which the second segment 42 is applied. For example, where the annuloplasty prosthesis 20 is configured for use in repairing a mitral valve annulus, the second segment 42 is applied to the anterior aspect of the mitral valve annulus. With this in mind, the imaging element 26, and thus the corresponding segment 42 of the annuloplasty prosthesis 20, will readily move or "flex" with normal movement of the anterior aspect of the mitral valve annulus. Alternatively, however, the imaging element 26 can have a more rigid construction and/or the second segment 42 of the annuloplasty prosthesis 20 can include additional components that otherwise serve to restrict flexation or movement of the corresponding segment 42 of the annuloplasty prosthesis 20.

The imaging element 26 can be formed of a variety of shapes and materials selected to satisfy the desired size and flexibility attributes described above, as well as exhibiting a desired radiopaque, echogenic and/or otherwise imaging enhancing characteristic (e.g., permits radiographic visualization of the imaging element 26 via known and future-developed techniques such as x-ray photographs, CAT scans, etc.). In one embodiment, the imaging element 26 is a barium sulfate-impregnated silicone strip. An appropriate barium sulfate-impregnated silicone strip can be formed by molding a mixture of barium sulfate and silicone medical adhesive to a desired shape and size. Other manufacturing techniques are equally acceptable. Even further, the material(s) selected for the imaging element 26 can assume a wide variety of other forms.

Figure 4A:
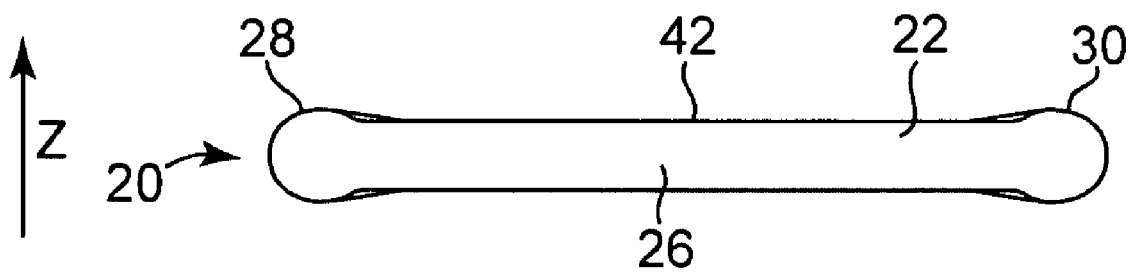
FIG. 4A is an end view of the annuloplasty prosthesis of FIG. 1 in a relatively flattened state.
Figure 4B:
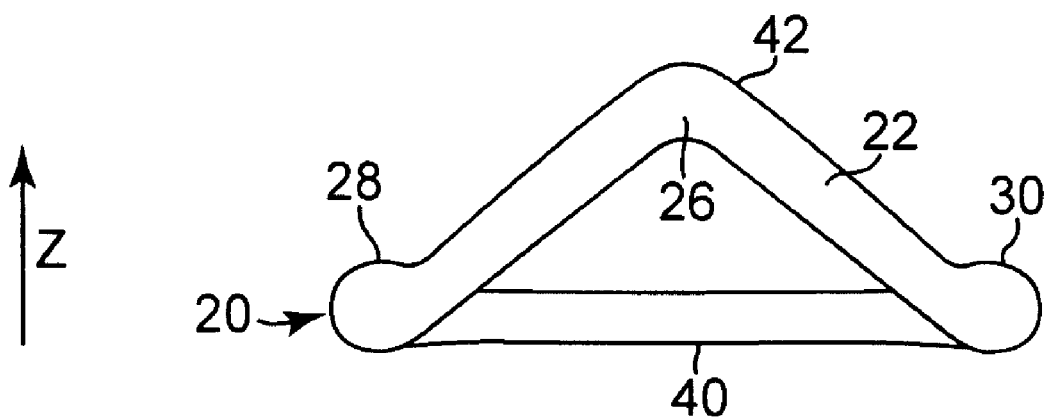
FIG. 4B is an end view of the annuloplasty prosthesis of FIG. 1 in a flexed state.

Flexibility of the imaging element 26 in accordance with some embodiments of the present invention is illustrated by a comparison of FIGS. 4A and 4B. In particular, FIG. 4A schematically illustrates an end view of the annuloplasty prosthesis 20, and in particular the second segment 42, in a natural or undeflected state. As shown, the second segment 42, and thus the imaging element 26 (referenced generally), is substantially flat (i.e., little or no variation in height or Z direction). As a point of reference, in other alternative embodiments, the annuloplasty prosthesis 20 can include one or more additional bodies within the sheath 22 along the second segment 42 that otherwise serve to impart a curvature in the Z direction in the natural state of the annuloplasty prosthesis 20. Further, the first region 40 (generally hidden in FIG. 4A, but seen in FIG. 4B) can also include or define a saddle shape (e.g., a curvature in the Z direction) as previously described. Regardless, the imaging element 26 exhibits sufficient flexibility to permit the second segment 42 to transition, move, or "flex" to the flexed state of FIG. 4B. For example, following implant and as described in greater detail below, the second segment 42 will be subjected to various forces as the valve annulus to which the annuloplasty prosthesis 20 is applied transitions in shape through systole and diastole. In connection with this movement, then, the imaging element 26, and thus the second segment 42, readily assumes the flexed orientation of FIG. 4B.

Figure 5A:
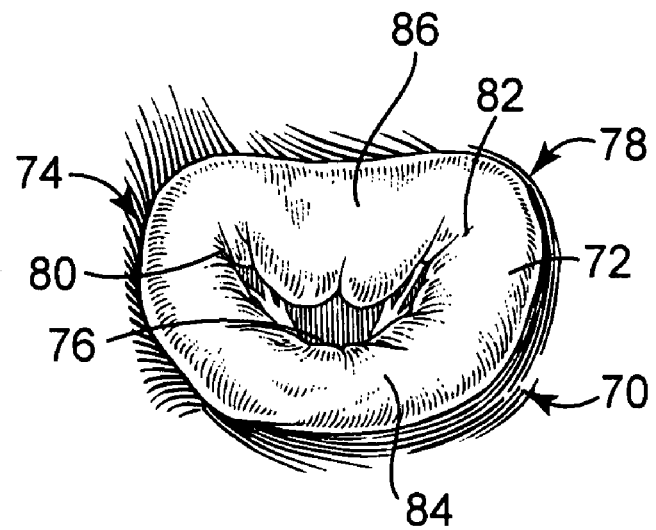
FIG. 5A illustrates a mitral valve anatomy.

The annuloplasty prosthesis 20 can be employed in the repair of various heart valves, particularly the atrio-ventricular valves. To this end, various instruments can be provided to assist in implanting the annuloplasty prosthesis 20, such as a holder, a sizer assembly, etc. In some embodiments, the annuloplasty prosthesis 20 is implanted to a mitral valve 70 the anatomy of which is shown in FIG. 5A. The mitral valve 70 includes a valve annulus 72, an antero-lateral trigone 74, a posterior leaflet 76, a postero-medial trigone 78, an inferior commissure 80, and a superior commissure 82. With these anatomical features in mind, the valve annulus 72 can be described as defining or being defined by a posterior aspect 84 and an anterior aspect 86.

Figure 5B:
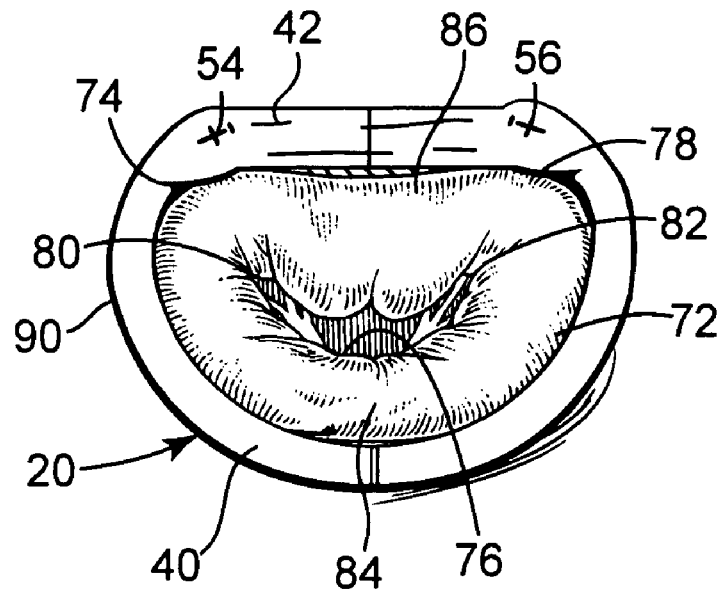
FIG. 5B is a top view of the annuloplasty prosthesis of FIG. 1 mounted on the valve annulus of the mitral valve of FIG. 5A.

Implantation of the annuloplasty prosthesis 20 to the mitral valve annulus 72 is shown in FIG. 5B. Implanting sutures 90 are used to connect the annuloplasty prosthesis 20 to the valve annulus 72. In accordance with some embodiments in which the stiffening element 24 (FIG. 1) forms the eyelets 54, 56 (referenced generally), one or more of the implanting suture(s) 90 are passed through the eyelet 54 and sewn to the antero-lateral trigone 74, whereas the implanting suture(s) 90 associated with the eyelet 56 are sewn to the postero-medial trigone 78. Regardless, the first segment 40 of the annuloplasty prosthesis 20 is applied to the posterior aspect 84 of the valve annulus 72, whereas the second segment 42 is applied to the anterior aspect 86. As previously described, the first segment 40, and in particular the stiffening element 24, serves to, in some embodiments, remodel the posterior aspect 84 to a desired shape. Conversely, the second segment 42 exhibits sufficient flexibility so as to permit natural movement of the anterior aspect 86. That is to say, the imaging element 26 (FIG. 1) does not impede natural movement of the anterior aspect 86 of the valve annulus 72.

Following implantation, radiographic, echogenic and/or image enhancing image(s) of the annuloplasty prosthesis 20, for examples, can be generated via various non-invasive techniques, with these images being used to evaluate a status of the valve 70, and in particular the valve annulus 72. For example, the radiographic image(s) of the annuloplasty prosthesis 20 will include an image of the imaging element 26 (FIG. 1) as otherwise connected to the anterior aspect 86 of the valve annulus 72. Because the imaging element 26 extends along at least a majority of the anterior aspect 86, the radiopaque, echogenic and/or image enhanced image(s) will reflect or illustrate a flexibility of the interior aspect 86 (e.g., when the valve 70 is at an end systole state, an end diastole state, etc.). Further, where the stiffening element 24 (FIG. 1) includes a radiopaque, echogenic and/or otherwise image enhanced component, the resultant radiographic, echogenic and/or other image enhanced image(s) will include a representation of a virtual entirety of the annuloplasty prosthesis 20 and thus of the valve annulus 72 to which the prosthesis 20 is mounted. Under these circumstances, then, the valve evaluation facilitated by the radiographic, echogenic and/or otherwise image enhanced image(s) can include a calculation of the orifice area established by the valve annulus 72 in various states. In yet other embodiments, the radiographic, echogenic and/or otherwise image enhanced image(s) will provide a clear indication that the implanted annuloplasty prosthesis 20 is akin to an annuloplasty ring (as opposed to an annuloplasty band) due to the clear presence of the imaging element 26 in the generated image(s).

The annuloplasty prosthesis in accordance with aspects of the present invention provides a marked improvement over previous designs. Inclusion of an imaging element along a substantive segment or region of the annuloplasty prosthesis facilitates obtaining of important anatomical information associated with the valve annulus being repaired via non-invasive, radiographic visualization techniques. Further, the imaging element promotes, in some embodiments, desired flexibility of the annuloplasty prosthesis along a desired region or segment of the prosthesis.

Although the present invention has been described with reference to preferred embodiments, workers skilled in the art will recognize that changes can be made in form and detail without departing from the spirit and scope of the present invention.

What is claimed is:

1. An annuloplasty prosthesis for repairing an atrial-ventricular valve having a valve annulus, the prosthesis comprising:
    a sheath;
    an arcuate stiffening element within the sheath, the stiffening element being elongate, having a maximum width and extending between discrete first and second ends that are turned back toward one another and that are separated by a lateral spacing, wherein the stiffening element is included in a first segment of the prosthesis that defines a majority of an arcuate annular shape of the annuloplasty prosthesis; and
    an imaging element disposed within and extending along at least a portion of the sheath that extends between the first and second ends of the stiffening element, the imaging element being an elongate strip, having a width and extending in the lateral spacing as the imaging element and the sheath extend directly between the first and second ends of the stiffening element without being curved, wherein the elongate strip as comprising the imaging element is greater in width than the maximum width of the stiffening element so that one extension of the elongate strip along the sheath is distinguishable from the stiffening element during an imaging process taken from a direction perpendicular to the arcuate annular shape of the annuloplasty prosthesis, and further wherein the imaging element is included in a second segment of the prosthesis, and the second segment is characterized as being more flexible than the first segment.

2. The annuloplasty prosthesis of claim 1, wherein the imaging element is a barium sulfate-impregnated strip.

3. The annuloplasty prosthesis of claim 1, wherein the imaging element is characterized as being more flexible than the stiffening element.

4. The annuloplasty prosthesis of claim 1, wherein the imaging element has a length that is at least 50% of a length defined by the lateral spacing.

5. The annuloplasty prosthesis of claim 1, wherein a first end of the imaging element is adjacent to, but spaced from, the first end of the stiffening element, and a second end of the imaging element is adjacent to, but spaced from, the second end of the stiffening element.

6. The annuloplasty prosthesis of claim 1, wherein the imaging element is rectangular.

7. The annuloplasty prosthesis of claim 1, wherein the stiffening element is circular in cross-section and the width of the imaging element is greater than a diameter of the stiffening element.

8. The annuloplasty prosthesis of claim 1, wherein the stiffening element includes a metal wire such that following implantation to the valve annulus, the stiffening element facilitates at least one of radiographic, echogenic and image enhancing imaging of the first segment of the prosthesis and the imaging element facilitates at least one of radiographic, echogenic and image enhanced imaging of the second segment of the annuloplasty prosthesis.

9. The annuloplasty prosthesis of claim 8, wherein the first segment corresponds to a posterior aspect of a mitral valve annulus, and the second segment corresponds to an anterior aspect of the mitral valve annulus.

10. The annuloplasty prosthesis of claim 1, further comprising:
    suture indicia formed on an exterior of the sheath in a segment of the annuloplasty prosthesis corresponding with the imaging element.

11. A method of implanting an annuloplasty prosthesis to an annulus of a heart valve of a patient, the method comprising:
    providing an annuloplasty prosthesis comprising:
        a sheath,
        an arcuate stiffening element within the sheath, the stiffening element being elongate, having a maximum width and extending between discrete first and second ends that are turned back toward one another and that are separated by a lateral spacing, wherein the stiffening element is included in a first segment of the prosthesis that defines a majority of an arcuate annular shape of the annuloplasty prosthesis,
        an imaging element disposed within and extending along at least a portion of the sheath that extends between the first and second ends of the stiffening element, the imaging element being an elongate strip, having a width and extending in the lateral spacing as the imaging element and the sheath extend directly between the first and second ends of the stiffening element without being curved, wherein the elongate strip as comprising the imaging element is greater in width than the maximum width of the stiffening element so that one extension of the elongate strip along the sheath is distinguishable from the stiffening element during an imaging process taken from a direction perpendicular to the arcuate annular shape of the annuloplasty prosthesis, and further wherein the imaging element is included in a second segment of the prosthesis, and the second segment is characterized as being more flexible than the first segment;
    implanting the annuloplasty prosthesis to the valve annulus;
    generating an image of the annuloplasty prosthesis including an image of the stiffening element and the wider imaging element by directing energy to the prosthesis and the valve annulus; and
    evaluating a status of the valve based upon the image generated.

12. The method of claim 11, wherein the evaluated status relates to a flexibility of the valve annulus.

13. The method of claim 11, wherein the evaluated status relates to an orifice area of the valve annulus.

14. The method of claim 11, wherein the generated image further includes an image of the stiffening element.

15. The method of claim 14, wherein the evaluated status relates to a calculated orifice area of the valve annulus based upon the image of the imaging element and the image of the stiffening element.

16. The method of claim 11, wherein the valve is a mitral valve, and further wherein the annuloplasty prosthesis defines an anterior segment along the imaging element and a posterior segment along the stiffening element, and further wherein implanting the annuloplasty prosthesis includes:

securing the anterior segment of the annuloplasty prosthesis to an anterior aspect of the mitral valve annulus; and securing the posterior segment of the annuloplasty prosthesis to a posterior aspect of the mitral valve annulus.

17. The method of claim 16, wherein the image generated of the imaging element is indicative of a flexibility of the anterior aspect of the mitral valve annulus.

* * * * *